United States Patent
August et al.

(10) Patent No.: US 8,329,669 B2
(45) Date of Patent: Dec. 11, 2012

(54) COMPOSITION AND METHOD FOR TREATMENT OF TUMORS

(75) Inventors: Paul August, Boxford, MA (US); Waan Jeng Huang, Lexington, MA (US); Sridaran Natesan, Ashland, MA (US); Soyan Lieberman, Solana Beach, CA (US)

(73) Assignee: Sanofi, Paris (FR)

( * ) Notice: Subject to any disclaimer, the term of this patent is extended or adjusted under 35 U.S.C. 154(b) by 524 days.

(21) Appl. No.: 12/304,818

(22) PCT Filed: Jul. 25, 2007

(86) PCT No.: PCT/US2007/074277
§ 371 (c)(1),
(2), (4) Date: Sep. 25, 2009

(87) PCT Pub. No.: WO2008/014296
PCT Pub. Date: Jan. 31, 2008

(65) Prior Publication Data
US 2010/0035807 A1    Feb. 11, 2010

Related U.S. Application Data

(60) Provisional application No. 60/833,879, filed on Jul. 28, 2006.

(51) Int. Cl.
*A61K 31/70* (2006.01)
*C07H 21/02* (2006.01)
*C07H 21/04* (2006.01)

(52) U.S. Cl. ........................ 514/44 A; 536/24.1; 536/24.5

(58) Field of Classification Search .................. 536/24.1, 536/24.3, 24.5
See application file for complete search history.

(56) References Cited

U.S. PATENT DOCUMENTS

| | | | |
|---|---|---|---|
| 4,797,368 A | 1/1989 | Carter et al. | |
| 4,861,719 A | 8/1989 | Miller | |
| 4,987,071 A | 1/1991 | Cech et al. | |
| 5,139,941 A | 8/1992 | Muyczka et al. | |
| 5,168,062 A | 12/1992 | Stinski et al. | |
| 5,385,839 A | 1/1995 | Stinski | |
| 5,459,127 A | 10/1995 | Felgner et al. | |
| 5,580,859 A | 12/1996 | Felgner et al. | |
| 5,589,466 A | 12/1996 | Felgner et al. | |
| 5,693,622 A | 12/1997 | Wolff et al. | |
| 6,150,092 A * | 11/2000 | Uchida et al. | 435/6.12 |
| 6,887,468 B1 * | 5/2005 | Thorpe et al. | 424/130.1 |

FOREIGN PATENT DOCUMENTS

| | | |
|---|---|---|
| CA | 2012311 | 6/2003 |
| EP | 0140308 | 10/1984 |
| EP | 0178220 | 4/1986 |

(Continued)

OTHER PUBLICATIONS

Samworth et al (Eur J Biochem, 1998, 171(1-2): Abstract).*

(Continued)

*Primary Examiner* — Terra Cotta Gibbs
(74) *Attorney, Agent, or Firm* — McDonnell Boehnen Hulbert & Berghoff LLP (57) ABSTRACT

The present invention relates to a composition which is useful in the treatment of a tumor, a method for making such a composition, and a method for using such a composition. The invention relates also to a method for assaying for inhibitors of the activity of Core 1 protein and/or other proteins of the respiratory complex III of mitochondria.

19 Claims, 5 Drawing Sheets

FOREIGN PATENT DOCUMENTS

| | | |
|---|---|---|
| EP | 0185573 A1 | 6/1986 |
| EP | 0453242 | 10/1991 |
| EP | 0488528 | 6/1992 |
| WO | WO89/07150 | 8/1989 |
| WO | WO90/02806 | 3/1990 |
| WO | WO91/18088 | 11/1991 |
| WO | WO92/15680 | 9/1992 |
| WO | WO93/08845 | 5/1993 |
| WO | WO93/09239 | 5/1993 |
| WO | WO94/12649 | 6/1994 |
| WO | WO94/26914 | 11/1994 |
| WO | WO94/28152 | 12/1994 |
| WO | WO94/28938 | 12/1994 |
| WO | WO95/02697 | 1/1995 |
| WO | WO95/21931 | 4/1995 |
| WO | WO95/18863 | 7/1995 |
| WO | WO96/01313 | 1/1996 |
| WO | WO96/25508 | 4/1996 |
| WO | WO96/13596 | 5/1996 |
| WO | WO96/17823 | 6/1996 |
| WO | WO2004/030615 | 4/2004 |
| WO | WO2005/003297 | 1/2005 |
| WO | WO2006/015047 | 2/2006 |

OTHER PUBLICATIONS

Adams et al., The c-myc oncogene driven by immunoglobulin enhancers induces lymphoid malignancy in transgenic mice, Nature, vol. 318, Dec. 12, 1985 p. 533-538.

Alexander et al., Expression of the c-myc Oncogene under Control of an Immunoglobulin Enhancer in EuL-myc Transgenic Mice, Mol. & Cell. Biol., vol. 7, No. 4, Apr. 1987, pp. 1436-1444.

Aza-Blanc et al., Identification of Modulators of TRAIL-Induced Apoptosis via RNAi-Based Phenotypic Screening, Mol. Cell, vol. 12, Sep. 2003, pp. 627-637.

Beard et al., Transcription Mapping of Mouse Adenovirus Tye 1 Early Region 3, Virology, vol. 175, 1990, pp. 81-90.

Bender et al., Evidence that the Packaging Signal of Moloney Murine Leukemia Virus Extends into the gag Region, J. of Virology, vol. 61, No. 5, May 1987, pp. 1639-1646.

Bernstein et al., Gene Transfer With Retrovirus Vectors, Genetic Engineering, vol. 7, 1985, pp. 235-261.

Burns et al., Identification of Inhibitors of TRAIL-induced Death (ITiDs) in the TRAIL sensitive Colon Carcinoma Cell Line SW480 Using a Genetic Approach, J. of Biol. Chem., vol. 276, No. 41, Oct. 12, 2001, pp. 37879-37886.

Collins at al., Reaction Conditions and Kinetics of Self-cleavage of a Ribozyme Derived from Neurospora VS RNA, Biochemistry, vol. 32, 1993, pp. 2795-2799.

Curiel at al., High Efficiency Gene Transfer Mediated by Adenovirus Coupled to DNA-Polylysine Complexes, Human Gene Therapy, vol. 3, 1992, pp. 147-154.

Felgner et al., Cationic liposome-mediated transfection, Nature, vol. 337, Jan. 1989, pp. 387-388.

Graham et al., Characteristics of a Human Cell Line Transformed by DNA from Human Adenovirus Type 5, J. Gen. Virol. vol. 36. 1977, pp. 59-72.

Graham et al., Covalently closed circles of human adenovirus DNA are infectious, EMBO Journal, vol. 3. No. 12, 1984, pp. 2917-2922.

Guerrier-Takada et al., The RNA Moiety to Ribonuclease P is the Catalytic Subunit of the Enzyme; Cell, vol. 35, Dec. 1983, pp. 849-857.

Grossschedl et al., Introduction of a u immunoglobulin Gene into the Mouse Germ Line: Specific Expression in Lymphoid Cells and Synthesis of Functioal Antibody, Cell, vol. 38, Oct. 1984, pp. 647-568.

Hammer et al., Diversity of Aipha-Fetoprotein Gene Expression in Mice Is Generated by a Combination of Separate Enhancer Elements, Science, vol. 235, Jan. 2, 1987. pp. 53-58.

Hampel et al., 'Hairpin' catalytic RNA model: evidence for helices and sequence requirement for substrate RNA, Nucl. Acids Res. vol. 18, No. 2, 1990, pp. 299-304.

Hampel et al., RNA Catalytic Properties of the Minimum (−)sTRSV Sequence, Biochemistry, vol. 28, 1989, pp. 4929-4933.

Hanahan, D., Heritable formation of pancreatic Beta-cell tumours in transgenic mice expressing recombinant insulin/simian virus 40 oncogenes, Nature, vol. 315, May 9, 1985, p. 115-122.

Hara et al., Synergistic enhancement of TRAIL- and tumor necrosis factor alpha induced cell death by a phenoxazine derivative, Mol. Cancer Ther. vol. 4, No. 7, Jul. 2005, pp. 1121-1127.

Islam et al., A complete cDNA sequence for core I protein subunit of human-ubiquinoi-cytochrome c reductase, Biochemistry and Molecular Biology International Apr. 1994. vol. 32, No. 5, pp. 797-805.

Kelsey et al., Species- and tissue-specific expression of human alpha1-antitrypsin in transgenic mice, Genes & Development, vol. 1, 1987, pp. 161-172.

Kollias et al., Regulated Expression of Human alpha-γ, Beta, and Hybrid γBeta Globin Genes in Transgenic Mice: Manipulation of the Developmental Expression Patterns, Cell, vol. 46, Jul. 4, 1986, pp. 89-94.

Kriaucionis et al., Gene Expression Analysis Exposes Mitochondrial Abnormalities in a Mouse Model of Rett Syndrome, Molecular and Cellular Biology, Jul. 2006, vol. 26, No. 13, pp. 5033-5042.

Krumlauf et al., Developmental Regulation of ox-Fetoprotein Genes in Transgenic Mice, Mol & Cell Biol., vol. 5, No. 7, Jul. 1985, pp. 1639-1648.

Leder et al., Consequences of Widespread Deregulation of the c-myc Gene in Transgenic Mice: Multiple Neoplasms and Normal Development, Cell, vol. 45, May 23,1986, pp. 485-495.

Levrero et al., Defective and nondefective adenovirus vectors for expressing foreign genes in vitor and in vivo; Gene, vol. 101, 1991, pp. 195-2002.

MacDonald, R.J., Expression of the Pancreatic Elastase I Gene in Transgenic Mice, Hepatology, vol. 7. No. 1, 1987, pp. 42S-51S.

Magram et al., Developmental Regulation of a cloned adult Beta-globin Gene in Transgenic Mice, Nature, vol. 315, May 23, 1985, p. 338-340.

Mark et al., Humanization of Monoclonal Antibodies, Handbook of Experimental Pharmacology, vol. 113, Chapter 4, 1994.

Mason et al., The Hypogonadal Mouse: Reproductive Functions Restored by Gene Therapy, Science, Vo. 284, Dec. 12, 1986, pp. 1372-1377.

McCormick, D., Huan Gene Therapy: The First Round, Biotechnology, vol. 3, No. 8, Aug. 1985, p. 689-693.

Ohkawa et al., Activities of HIV-RNA targeted ribozymes transcribed from a shot-gun type ribozyme-trimming plasmid. Nucleic Acids Symp, Ser., vol. 27, 1992, pp. 15-16.

Ornitz et al., Elastase I Promoter Directs Expression of Human Growth Hormone and SV40 T Antigen Genes to Pancreatic Acinar Cells in Transgenic Mice, Cold Spring Harbor Symp. Quant Biol., vol. 50, 1986pp. 399-409.

Perrotta et al., Cleavage of Oligoribonucleotides by a Ribozyme Derived from the Hepatitis Virus RNA Sequence, Biochemistry, vol. 31, 1992, pp. 16-21.

Pinkert et al., An a1bumin enhancer located 10 kb uptream functions along with its promoter to d1rect eff1cient 1iver-specific expression 1n transgenic mice, Genes & Development, vol. 1, 1987, pp. 268-276.

Raven Press, Lentiviruses,, Fields Virology, 2nd Ed., vol. 22, Ch. 55, 1990 pp. 1571-1589.

Readhead et al., Expression of a Myelin Basic Protein Gene in Transgenic Shiverer Mice: Correction of the Dysmyelinating Phenotype, Cell, vol. 48, Feb. 27, 1987, pp. 703-712.

Rossi et al., Ribozymes as Anti-HIV-1 Therapeutic Agents: Principles, Applications and Problems, AIDS Research and Human Retroviruses, vol. 8, No. 2, 1992, pp. 183-190.

Saville et al., A Site-Specific Self-Cleavage Reaction Performed by a Novel RNA in Neurospora Mitochondria. Cell, vol. 61, May 18, 1990, pp. 685-696.

Saville et al., RNA-mediated ligation of self-cleavage product of a Neurospora mitochondrial plasmid transcript, PNAS, vol. 88, Oct. 1991, pp. 8826-8830.

Shani et al., Tissue-specific expression of rat myosin light-chain 2 gene in transgenic mice, Nature, vol. 314, Mar. 21,1985, pp. 283-286.

Swift et al., Tissue-Specific Expression of the Rat Pancreatic Elastase 1 Gene in transgenic mice, Cell, vol. 38, Oct. 1984, pp. 639-646.

Taira et al., Construction of a novel RNA-transcript-trimming plasmid which can be used both in vitro in place of run-off and (G)-free transcriptions and in vivo as multi-sequences transcription vectors, Nucleic Acids Res. No. 19, 1991, pp. 5125-5130.

Ventura et al., Activation of HIV-specific ribozyme activity by self-cleavage, Nucleic Acids Res., vol. 21, No. 14, 1993, pp. 3249-3255.

Williams et al., Introduction of foreign genes into tissues of living mice by DNA-coated microprojectiles, PNAS, vol. 88, Apr. 1991, pp. 2726-2730.

Wilson et al., Hepatocyte-directed Gene Transferi n Vivo Leads to Transient Improvement of Hypercholesterolemia in Low Density Lipoprotein Receptor-deficient Rabbits, J. of Biol. Chem., vol. 267, No. 2, Jan. 15, 1992 pp. 963-967.

Wu et al., Receptor-mediated Gene Delivery and Expression in Vivo, J. of Biol. Chem., vol. 263, No. 29, Oct. 15, 1988, pp. 14621-14624.

Wu et al., Receptor-mediated in Vitro Gene Transformation by a Soluble DNA Carrier System, J. of Biol. Chem., vol. 262, No. 10, Apr. 5, 1987, pp. 4429-4432.

International Search Report in International Application No. PCT/US2007/074277, mailed Jul. 30, 2008.

International Preliminary Report on Patentability in International Application No. PCT/US2007/074277, report issued Feb. 3, 2009.

Elbashir et al., "Analysis of gene function in somatic mammalian cells using small interfering RNAs," Methods 26: 199-213 (2002).

* cited by examiner

| Tissue | Tumor | Fold upregulation over normal tissue |
|---|---|---|
| Bone | Giant Cell Tumor of Bone | 2.4 |
| | Osteosarcoma | 1.8 |
| Endometrium | Mullerian Mixed Tumor | 1.7 |
| Kidney | Carcinoma | 1.2 |
| Lung | Adenosquamous Carcinoma | 1.6 |
| | Neuroendocrine Carcinoma (Non-Small Cell Type) | 2.2 |
| Ovary | Mullerian Mixed Tumor | 1.5 |
| Pancreas | Islet Cell Tumor | 1.4 |
| Skin | Malignant Melanoma | 1.5 |

Nucleic Acid Sequence of human UQCRC1 (Core 1)

NM_003365        1636 bp    mRNA
Homo sapiens ubiquinol-cytochrome c reductase core protein I (UQCRC1), mRNA.

SEQ ID NO:1

```
   1 cagtctacgc ttgcgcggcg caacagggcc gactgcagct ggaagatggc ggcgtccgtg
  61 gtctgtcggg ccgctaccgc cggggcacaa gtgctattgc gcgcccgccg ctcgccggcc
 121 ctgctgcgga cgccagcctt gcggagtacg gcaaccttcg ctcaggcgct ccagttcgtg
 181 ccggagacgc aggttagcct gctggacaac ggcctgcgtg tggcctccga gcagtcctct
 241 cagcccactt gcacggtggg agtgtggatt gatgttggca ccgttttga gactgagaag
 301 aataatgggg caggctactt tttggagcat ctggctttca agggaacaaa gaatcggcct
 361 ggcagtgccc tggagaagga ggtggagagc atggggcc atcttaatgc ctacagcacc
 421 cggagcaca cagttacta catcaaggcg ctgtccaagg atctgccgaa agctgtggag
 481 ctcctgggtg acattgtgca gaactgtagt ctggaagact cacagattga aaggaacgt
 541 gatgtgatcc tgcgggagat gcaggagaat gatgcatcta tgcgagatgt ggtctttaac
 601 tacctgcatg ccacagcatt ccagggcaca cctctagcc aggctgtgga gggcccagt
 661 gagaatgtca ggaagctgtc tcgtgcagac ttgaccgagt acctcagcac acattacaag
 721 gcccctcgaa tggtgctggc agcagctgga ggagtggagc accagcaact gttagacctc
 781 gccagaagc acctcgtgg catccatgg acatatgcag aggacgctgt gccactctt
 841 actccatgcc gcttcactgg cagtgagatc cgccaccgtg atgatgctct acctttgcc
 901 cacgtggcca ttgcagtaga gggtcctggc tgggccagcc cggacaatgt ggccttgcaa
 961 gtggccaatg ccatcatcgg ccactatgac tgcacttatg gtggtggcgt gcacctgtcc
1021 agcccactgg cttcaggtgc tgtggccaac aagctatgcc agagtttcca gaccttcagc
1081 atctgctatg cagagacggg cttgctgggt gcacactttg tctgtgaccg aatgaaaatc
1141 gatgacatga tgttcgtcct gcaaggcag tggatgcgcc tgtgtaccag tgccacggag
1201 agtgaggtgg cccggggcaa aaacatcctc agaaatgccc tggtatctca tctagatggc
1261 actactcctg tgtgtgagga catcggacgc agcctactga ctatggcg ccgcatccc
1321 ctggctgaat gggaaagccg gattgcggag gtggatgcca gtgtggtacg tgagatctgc
1381 tccaagtaca tctatgacca gtgcccagca gtggctggat atggcccat tgagcagctc
1441 ccagactaca accggatccg tagcggcatg ttctggctgc gcttctaggc gggaagccta
1501 tgtaagcaag agggcaggc cggggtttgt ggtccccc ccaccacaaa cacagcactt
1561 cggctcctct aacctgtgcc acaggtgacc accaataaaa tcctctgctg agaagtgaaa
1621 aaaaaaaaaa aaaaaa
```

FIG. 5A

Complete amino acid sequence of human UQCRC1:

SEQ ID NO:2

```
translation="MAASVVCRAATAGAQVLLRARRSPALLRTPALRSTATFAQALQF
    VPETQVSLLDNGLRVASEQSSQPTCTVGVWIDVGSRFETEKNNGAGYFLEHLAFKGTK
    NRPGSALEKEVESMGAHLNAYSTREHTAYYIKALSKDLPKAVELLGDIVQNCSLEDSQ
    IEKERDVILREMQENDASMRDVVFNYLHATAPQGTPLAQAVEGPSENVRKLSRADLTE
    YLSTHYKAPRMVLAAAGGVEHQQLLDLAQKHLGGIPWTYAEDAVPTLTPCRFTGSEIR
    HRDDALPFAHVAIAVEGPGWASPDNVALQVANAIIGHYDCTYGGVHLSSPLASGAVA
    NKLCQSFQTFSICYAETGLLGAHFVCDRMKIDDMMFVLQGQWMRLCTSATESEVARGK
    NILRNALVSHLDGTTPVCEDIGRSLLTYGRRIPLAEWESRIAEVDASVVREICSKYIY
    DQCPAVAGYGPIEQLPDYNRIRSGMFWLRF"
```

FIG. 5B

SEQUENCE LISTING

```
<160> NUMBER OF SEQ ID NOS: 3

<210> SEQ ID NO 1
<211> LENGTH: 1636
<212> TYPE: DNA
<213> ORGANISM: Homo sapiens

<400> SEQUENCE: 1
cagtctacgc ttgcgcggcg caacagggcc gactgcagct ggaagatggc ggcgtccgtg      60
gtctgtcggg ccgctaccgc cggggcacaa gtgctattgc gcgcccgccg ctcgccggcc     120
ctgctgcgga cgccagcctt gcggagtacg gcaaccttcg ctcaggcgct ccagttcgtg     180
ccggagacgc aggttagcct gctggacaac ggcctgcgtg tggcctccga gcagtcctct     240
```

```
cagcccactt gcacggtggg agtgtggatt gatgttggca gccgttttga gactgagaag    300
aataatgggg caggctactt tttggagcat ctggctttca agggaacaaa gaatcggcct    360
ggcagtgccc tggagaagga ggtggagagc atgggggccc atcttaatgc ctacagcacc    420
cgggagcaca cagcttacta catcaaggcg ctgtccaagg atctgccgaa agctgtggag    480
ctcctgggtg acattgtgca gaactgtagt ctggaagact cacagattga aaggaacgt     540 gatgtgatcc tgcgggagat gcaggagaat gatgcatcta tgcgagatgt ggtctttaac    600
tacctgcatg ccacagcatt ccagggcaca cctctagccc aggctgtgga ggggcccagt    660
gagaatgtca ggaagctgtc tcgtgcagac ttgaccgagt acctcagcac acattacaag    720
gcccctcgaa tggtgctggc agcagctgga ggagtggagc accagcaact gttagacctc    780
gcccagaagc acctcggtgg catcccatgg acatatgcag aggacgctgt gcccactctt    840
actccatgcc gcttcactgg cagtgagatc cgccaccgtg atgatgctct accttttgcc    900
cacgtggcca ttgcagtaga gggtcctggc tgggccagcc ggacaatgt ggccttgcaa     960 gtggccaatg ccatcatcgg ccactatgac tgcacttatg gtggtggcgt gcacctgtcc   1020
agcccactgg cttcaggtgc tgtggccaac aagctatgcc agagtttcca gaccttcagc   1080
atctgctatg cagagacggg cttgctgggt gcacactttg tctgtgaccg aatgaaaatc   1140
gatgacatga tgttcgtcct gcaagggcag tggatgcgcc tgtgtaccag tgccacggag   1200
agtgaggtgg cccggggcaa aaacatcctc agaaatgccc tggtatctca tctagatggc   1260
actactcctg tgtgtgagga catcggacg agcctcctga cctatggccg ccgcatcccc   1320
ctggctgaat gggaaagccg gattgcggag gtggatgcca gtgtggtacg tgagatctgc   1380
tccaagtaca tctatgacca gtgcccagca gtggctggat atggccccat tgagcagctc   1440
ccagactaca accggatccg tagcggcatg ttctggctgc gcttctaggc gggaagccta   1500
tgtaagcaag agggcagggc cggggtttgt ggtcccccc ccaccacaaa cacagcactt    1560
cggctcctct aacctgtgcc acaggtgacc accaataaaa tcctctgctg agaagtgaaa   1620
aaaaaaaaaa aaaaaa                                                    1636
```

<210> SEQ ID NO 2
<211> LENGTH: 480
<212> TYPE: PRT
<213> ORGANISM: Homo sapiens

<400> SEQUENCE: 2

```
Met Ala Ala Ser Val Val Cys Arg Ala Ala Thr Ala Gly Ala Gln Val
 1               5                   10                  15

Leu Leu Arg Ala Arg Arg Ser Pro Ala Leu Leu Arg Thr Pro Ala Leu
             20                  25                  30

Arg Ser Thr Ala Thr Phe Ala Gln Ala Leu Gln Phe Val Pro Glu Thr
         35                  40                  45

Gln Val Ser Leu Leu Asp Asn Gly Leu Arg Val Ala Ser Glu Gln Ser
     50                  55                  60

Ser Gln Pro Thr Cys Thr Val Gly Val Trp Ile Asp Val Gly Ser Arg
 65                  70                  75                  80

Phe Glu Thr Glu Lys Asn Asn Gly Ala Gly Tyr Phe Leu Glu His Leu
                 85                  90                  95

Ala Phe Lys Gly Thr Lys Asn Arg Pro Gly Ser Ala Leu Glu Lys Glu
            100                 105                 110

Val Glu Ser Met Gly Ala His Leu Asn Ala Tyr Ser Thr Arg Glu His
        115                 120                 125
```

```
Thr Ala Tyr Tyr Ile Lys Ala Leu Ser Lys Asp Leu Pro Lys Ala Val
            130                 135                 140

Glu Leu Leu Gly Asp Ile Val Gln Asn Cys Ser Leu Glu Asp Ser Gln
145                 150                 155                 160

Ile Glu Lys Glu Arg Asp Val Ile Leu Arg Glu Met Gln Glu Asn Asp
                165                 170                 175

Ala Ser Met Arg Asp Val Val Phe Asn Tyr Leu His Ala Thr Ala Phe
            180                 185                 190

Gln Gly Thr Pro Leu Ala Gln Ala Val Glu Gly Pro Ser Glu Asn Val
            195                 200                 205

Arg Lys Leu Ser Arg Ala Asp Leu Thr Glu Tyr Leu Ser Thr His Tyr
210                 215                 220

Lys Ala Pro Arg Met Val Leu Ala Ala Ala Gly Gly Val Glu His Gln
225                 230                 235                 240

Gln Leu Leu Asp Leu Ala Gln Lys His Leu Gly Gly Ile Pro Trp Thr
                245                 250                 255

Tyr Ala Glu Asp Ala Val Pro Thr Leu Thr Pro Cys Arg Phe Thr Gly
            260                 265                 270

Ser Glu Ile Arg His Arg Asp Asp Ala Leu Pro Phe Ala His Val Ala
            275                 280                 285

Ile Ala Val Glu Gly Pro Gly Trp Ala Ser Pro Asp Asn Val Ala Leu
290                 295                 300

Gln Val Ala Asn Ala Ile Ile Gly His Tyr Asp Cys Thr Tyr Gly Gly
305                 310                 315                 320

Gly Val His Leu Ser Ser Pro Leu Ala Ser Gly Ala Val Ala Asn Lys
                325                 330                 335

Leu Cys Gln Ser Phe Gln Thr Phe Ser Ile Cys Tyr Ala Glu Thr Gly
            340                 345                 350

Leu Leu Gly Ala His Phe Val Cys Asp Arg Met Lys Ile Asp Asp Met
            355                 360                 365

Met Phe Val Leu Gln Gly Gln Trp Met Arg Leu Cys Thr Ser Ala Thr
            370                 375                 380

Glu Ser Glu Val Ala Arg Gly Lys Asn Ile Leu Arg Asn Ala Leu Val
385                 390                 395                 400

Ser His Leu Asp Gly Thr Thr Pro Val Cys Glu Asp Ile Gly Arg Ser
                405                 410                 415

Leu Leu Thr Tyr Gly Arg Arg Ile Pro Leu Ala Glu Trp Glu Ser Arg
            420                 425                 430

Ile Ala Glu Val Asp Ala Ser Val Arg Glu Ile Cys Ser Lys Tyr
            435                 440                 445

Ile Tyr Asp Gln Cys Pro Ala Val Ala Gly Tyr Gly Pro Ile Glu Gln
            450                 455                 460

Leu Pro Asp Tyr Asn Arg Ile Arg Ser Gly Met Phe Trp Leu Arg Phe
465                 470                 475                 480

<210> SEQ ID NO 3
<211> LENGTH: 99
<212> TYPE: PRT
<213> ORGANISM: Mus musculus

<400> SEQUENCE: 3

Met Ala Ala Ser Ala Val Cys Arg Ala Ala Cys Ser Gly Thr Gln Val
1               5                   10                  15

Leu Leu Arg Thr Arg Arg Ser Pro Ala Leu Leu Arg Leu Pro Ala Leu
            20                  25                  30
```

-continued

```
Arg Gly Thr Ala Thr Phe Ala Gln Ala Leu Gln Ser Val Pro Glu Thr
        35              40              45

Gln Val Ser Ile Leu Asp Asn Gly Leu Arg Val Ala Ser Glu Gln Ser
    50              55              60

Ser His Ala Thr Cys Thr Val Gly Val Trp Ile Asp Ala Gly Ser Arg
65              70              75              80

Tyr Glu Thr Glu Lys Asn Asn Gly Ala Gly Tyr Phe Leu Glu His Leu
                85              90              95

Ala Phe Lys
```

COMPOSITION AND METHOD FOR TREATMENT OF TUMORS

FIELD OF THE INVENTION

A tumor is an abnormal growth of tissue which may be malignant or benign. A benign tumor grows only locally whereas a malignant tumor spreads to other tissues.

Cancer is a genetic disease. The ability to resist apoptosis is a hallmark of cancer cells. Many genetic lesions are known to confer resistance to programmed cell death (apoptosis) in cancer cells. During apoptosis, enzymes called caspases carry out the process of breaking down the cell. Initiator caspases cleave inactive pro-forms of effector caspases, thus activating them. The activated effector caspases then proceed to cleave proteins within the cell. In normal tissue, the rate of apoptosis balances the rate of cellular growth in the tissue, thus regulating the growth of the tissue. If the apoptotic process of a cell is disturbed, the cell may continue to divide, thus leading to uncontrolled tissue growth.

Tumor Necrosis Factor-Related Apoptosis Inducing Ligand (TRAIL) is a promising therapeutic reagent for the treatment tumors. TRAIL is a member of the Tumor Necrosis Factor (TNF) superfamily which includes the potent apoptotic inducers TNF and Fas Ligand (FasL). TRAIL is of particular interest not only because it induces rapid apoptosis in a wide variety of human tumors and cancer cell lines, but it exhibits also little toxicity to normal cells and tissues TRAIL is normally expressed by many tissues within the body, but may also be administered exogenously during the treatment of a tumor. Injection of a soluble active form of TRAIL into mice bearing solid tumors induced apoptosis, suppressed tumor progression and improved survival. There is also evidence that combined treatment using TRAIL and various chemotherapeutic drugs can further increase tumor regression.

TRAIL binds to death receptors DR4 and DR5 on tumors and cancer cell lines and rapidly and specifically induces apoptosis. The binding of TRAIL to a death receptor induces either or both the extrinsic and intrinsic apoptotic pathways(s), depending upon the cell type. In both pathways, the binding of TRAIL to its receptor creates the binding site for an adaptor protein FADD (Fas Associated protein with Death Domain), which recruits and activates the initiator caspase 8. In some cells caspase 8 activates the extrinsic apoptotic pathway, leading directly to the activation of effector caspases 3, 6, and 7, sufficient to induce apoptosis. TRAIL may also induce apoptosis by the intrinsic pathway, where activation of caspase 8 initiates apoptosis involving the mitochondria and the formation of the apoptosome. Caspase 8 cleaves Bcl-2 inhibitory BH3-domain-containing protein (Bid), causing the truncated Bid to translocate from the cytoplasm to the outer membrane of the mitochondria and induce the oligomerization of Bax and Bak. The pores formed by Bax (Bcl-2-associated X protein) and Bak (Bcl-2-antagonist/killer 1) cause the loss of mitochondrial membrane polarization and release of cytochrome c, resulting in the metabolic failure of the cell's mitochondria. Cytochrome c in the cytoplasm then interacts with caspase 9 to activate the downstream effector caspases 3, 6 and 7.

Treatment using members of the TNF superfamily has, however, some limitations in that various tumor cells are resistant to apoptosis induced by members of the TNF superfamily, including TRAIL. The present invention addresses such limitations.

Reported Developments

It is known that certain molecules present in the body can function in a manner such that they suppress the activity of members of the TNF superfamily (such compounds are referred to herein as "TNF suppressors"). For example, it has been reported that cellular FLICE-inhibitory protein (c-FLIP$_s$), Bax inhibitor 1, and Bcl-X$_L$ suppress the apoptotic activity of TRAIL. Burns, T. F. and W. S. El-Deiry, J. Biol. Chem., 276: 37879-37886 (2001). It has been reported also that the genes AKT and MIRSA also suppress the apoptotic activity of TRAIL. See, e.g., Aza-Blanc et al., Molecular Cell, 12: 627-637 (2003).

It is known also that biological molecules which inhibit the activity of a TNF suppressor serve to sensitize a cell in a manner which improves the apoptotic activity of TRAIL. For example, the administration of siRNAs to target the genes AKT and MIRSA in a cell has been shown to sensitize the cell to the apoptotic activity of TRAIL. See, e.g., Aza-Blanc et al., Molecular Cell, 12: 627-637 (2003).

The present invention relates to the provision of means which function also to improve the apoptotic activity of TRAIL.

SUMMARY OF THE INVENTION

The present invention relates to a composition comprising: (A) an inhibitor which inhibits the activity of a Complex III protein, for example Core 1; and (B) a carrier.

In addition, the invention relates to a method for making a composition which comprises an inhibitor that inhibits the activity of a Complex III protein, for example Core 1, and a carrier comprising mixing said inhibitor with said carrier.

In another aspect, the invention relates to a method for making a composition which comprises an inhibitor that inhibits the activity of a Complex III protein, for example Core 1, a carrier, and a member of the tumor necrosis factor superfamily comprising mixing said inhibitor, said carrier, and said member.

A further aspect of the present invention relates to a method for conducting an assay to determine whether a compound is an inhibitor of TNF-suppressing activity of a Complex III protein, for example, Core 1, comprising comparing the viability of cells expressing the Complex III protein that have been grown in the presence of a member of the TNF superfamily and that have been contacted with said compound with the viability of cells from the same cell line that also express said Complex III protein, that have been grown in the absence of a member of the TNF superfamily and that have been contacted with said compound.

Yet another aspect of the present invention relates to a method for conducting an assay to determine whether a compound is an inhibitor of the TNF-suppressing activity of a Complex III protein, for example, Core 1, comprising: contacting the compound with cells that express said protein and that have been grown in the presence of a member of the TNF superfamily for a predetermined amount of time; contacting the compound with cells from the same cell line as those above that express the protein and that have been grown in the absence of a member of the TNF superfamily for the same predetermined amount of time; and comparing the viability of the cells.

Yet a further aspect of the present invention relates to a method for conducting an assay to determine whether a compound is an inhibitor of the activity of a Complex III protein, for example, Core 1, comprising: growing cells expressing the protein from a cell line in the presence of a member of the TNF superfamily; growing cells expressing the protein from the same cell line in the absence of a member of the TNF superfamily; and contacting the compound with the cells; and, after a predetermined period of time, comparing the viability of the cells.

A further additional aspect of the present invention relates to a method for conducting an assay to determine whether a compound is an inhibitor of TNF-suppressing activity of a Complex III protein, for example, Core 1, comprising comparing the viability of cells that express said protein and that have been contacted with both a member of the TNF superfamily and the compound with the viability of cells from the same cell line that express the protein and that have been contacted with the compound but not with a member of the TNF superfamily.

A further additional aspect of the present invention relates to a method for conducting an assay to determine whether a compound is an inhibitor of the TNF-suppressing activity of a Complex III protein, for example, Core 1, comprising: contacting cells which express the protein from a cell line with a member of the TNF superfamily and said compound; contacting cells which express the protein from the same cell line with the compound but not with a member of the TNF superfamily; and comparing the viability of the cells.

DESCRIPTION OF THE DRAWINGS

FIG. 5A shows the nucleic acid sequence of human UQCRC1 cDNA (SEQ ID NO: 1).

FIG. 5B shows the amino acid sequence of human Core 1 (SEQ ID NO: 2).

DETAILED DESCRIPTION OF THE INVENTION

The present invention involves the use of an inhibitor which inhibits the TNF-suppressing activity of a protein which is a member of mitochondrial respiratory complex III. For convenience, such a protein is referred to herein as a "Complex III" protein. The invention is applicable to the protein in a form in which it is associated with complex III as well as to the protein when it is in a form in which it is not associated with complex III, for example, in an insolated form. In an embodiment of the invention, the Complex III protein is Core 1.

The composition of the present invention comprises a pharmaceutically-effective amount of an inhibitor which inhibits the TNF-suppressing activity of a Complex III protein, for example Core 1. Essentially any compound which is capable of inhibiting the TNF-suppressing activity of a Complex III protein, for example Core 1, may be used in the practice of the present invention. Examples of compounds that may be employed in the practice of the present invention include: an antisense nucleic acid which inhibits the expression of the gene encoding a Complex III protein, for example Core 1; a nucleic acid which encodes an antisense nucleic acid which inhibits the expression of the gene a Complex III protein, for example Core 1; an siRNA which inhibits the expression of the gene encoding a Complex III protein, for example Core 1; a nucleic acid which encodes such an siRNA; an antibody that is capable of binding to and lowering the activity of a Complex III protein, for example Core 1; a nucleic acid which encodes an antibody which is capable of binding to and lowering the TNF-suppressing activity of a Complex III protein, for example Core 1; a ribozyme which is capable of lowering the expression of a Complex III protein, for example Core 1; a nucleic acid which encodes a ribozyme that is capable of lowering the expression of a Complex III protein, for example Core 1; and a small molecule compound which is capable of lowering the TNF-suppressing activity of a Complex III protein, for example Core 1.

The inhibitor is present in the composition in a concentration effective to inhibit the TNF-suppressing activity of a Complex III protein, for example Core 1. This may be determined by those of ordinary skill in the art, taking into account that effective concentrations will vary depending on the particular inhibitor used and the amounts and nature of other components of the composition. For guideline purposes, it is believed most applications will involve the use of the inhibitor in an amount of about 0.01% to about 15% by weight of the composition. In some embodiments, the inhibitor is present in an amount of about 0.01% to about 10% by weight of the composition, or about 0.1% to about 5% by weight of the composition.

In embodiments in which an antisense nucleic acid is used as an inhibitor, the antisense nucleic acid hybridizes with at least part of the deoxyribonucleic nucleic acid (DNA) encoding a Complex III protein, for example Core 1, to thereby inhibit the expression of the protein. The antisense nucleic acid may also be one which decreases the expression of the gene encoding a Complex III protein, for example Core 1, by inhibiting splicing of its primary transcript. The antisense nucleic acid may comprise DNA or ribonucleic acid (RNA) or both. Any length of antisense sequence is suitable for practice of the invention provided that it is capable of inhibiting the expression of a Complex III protein, for example Core 1. Preferably, the antisense sequence is at least 20 nucleotides in length. In preferred embodiments, the antisense nucleic acid is an oligonucleotide.

The antisense nucleic acids can be prepared synthetically, for example, by expression of all or part of a nucleic acid encoding a Complex III protein, for example Core 1, in the opposite orientation, as described in European Patent No. 140308. The sequence for the nucleic acid encoding Core 1 is provided in FIG. 5A. The preparation and use of synthetic antisense nucleic acids are described generally in International Application Publication No. WO 92/15680.

The antisense nucleic acid may be chemically modified, for example, to improve stability and/or selectivity. For example, one such modification involves the use of a sulfur group to replace the free oxygen of the phosphodiester bond, thus creating a phosphorothioate linkage. Phosphorothioate antisense nucleic acids are water soluble, polyanionic, and resistant to endogenous nucleases. In addition, antisense nucleic acids with phosphoramidite and polyamide (peptide) linkages can be synthesized. Such nucleic acids are typically very resistant to nuclease degradation. Furthermore, chemical groups can be added to the 2' carbon of the sugar moiety and the 5 carbon (C-5) of pyrimidines to enhance the stability of the antisense nucleic acid and facilitate the binding of the antisense nucleic acid to its target site. Modifications may include 2' deoxy, O-pentoxy, O-propoxy, O-methoxy, fluoro, methoxyethoxy phosphoro-thioates, modified bases, as well as other modifications known to those of skill in the art.

The antisense nucleic acid is present in the composition in a concentration effective to inhibit the expression of the nucleic acid encoding a Complex III protein, for example Core 1.

In embodiments in which a nucleic acid that encodes an antisense nucleic acid is used as an inhibitor, the nucleic acid is one which encodes an antisense nucleic acid of the type described above. The nucleic acid is present in the composition in a concentration effective to express an amount of antisense nucleic acid effective in inhibiting the expression of a Complex III protein, for example Core 1.

In embodiments in which an siRNA (small interfering RNA) is used as an inhibitor, the siRNA hybidizes with a portion of the mRNA encoding a Complex III protein, for example Core 1, and is capable of being incorporated into an RNA-induced silencing complex (RISC) which identifies and inhibits the expression of the mRNA. The siRNA is present in the composition in a concentration effective to inhibit the expression of the nucleic acid encoding the protein.

In another embodiment of the present invention, a nucleic acid encoding the above siRNA may be used as an inhibitor.

In embodiments in which an antibody is used as an inhibitor, the antibody is one which binds to Core 1 and inhibits the TNF-suppressing activity thereof. For example, the antibody can be monoclonal or polyclonal, chimeric, a Fab fragment, an Fv fragment, or a product of a Fab or Fv expression library.

Polyclonal antibodies can be prepared against an antigenic fragment of the Complex III protein, for example Core 1, or the intact protein. Monoclonal antibodies may be prepared, for example, using the method of Mishell, B. B., et al., Selected Methods in Cellular Immunology, (W. H. Freeman, ed.) San Francisco (1980). The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, and the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. G. E. Mark and E. A. Padlan, "Chapter 4. Humanization of Monoclonal Antibodies", The Handbook of Experimental Pharmacology Vol. 113, Springer-Verlag, New York, 1994). Transgenic animals may be used to express humanized antibodies.

The antibody may be a single chain antibody. Techniques known in the art for the production of single chain antibodies can be adapted to produce single chain antibodies to a Complex III protein, for example Core 1.

The antibody is present in the composition in a concentration effective to inhibit the activity of the Complex III protein, for example Core 1.

In embodiments in which a nucleic acid that encodes antibody is used as an inhibitor, the nucleic acid is one which encodes an antibody that binds to a Complex III protein, for example Core 1, and inhibits the activity thereof. The nucleic acid is present in the composition in a concentration effective to express an amount of antibody effective in inhibiting the activity of the protein.

In embodiments in which a ribozyme (ribonucleic acid enzyme) is used as an inhibitor, the ribozyme is one which contains both a catalytic domain and a substrate binding domain. The substrate binding domain is one which hybridizes with at least part of an mRNA encoding a Complex III protein, for example Core 1. The catalytic domain is one which is capable of cleaving the mRNA.

In preferred embodiments of this invention, the ribozyme is formed in a hammerhead motif. Other forms include a hairpin motif, a hepatitis delta virus, group I intron or RnaseP RNA (in association with an RNA guide sequence) motif or Neurospora VS RNA motif. Hammerhead motifs are described by Rossi et al., Aids Research and Human Retroviruses, 8: 183 (1992). Hairpin motifs are described in Hampel and Tritz Biochemistry, 28: 4929 (1989), and Hampel et al., Nucleic Acids Res., 18: 299 (1990). The hepatitis delta virus motif is described by Perrotta and Been, Biochemistry, 31: 16 (1992), the RnaseP motif is described by Guerrier-Takada et al., Cell, 35: 849 (1983), the Neurospora VS RNA ribozyme motif is described by Collins (Saville and Collins, Cell, 61: 685-696 (1990); Saville and Collins, Proc. Natl. Acad. Sci. USA, 88: 8826-8830 (1991); Collins and Olive, Biochemistry, 32, 2795-2799 (1993) the Group I intron motif is described by Cech et al., U.S. Pat. No. 4,987,071.

One exemplary method for preparing a ribozyme is to synthesize chemically an oligodeoxyribonucleotide with a ribozyme catalytic domain (~20 nucleotides) flanked by sequences that hybridize to the target Core 1 mRNA after transcription. The oligodeoxyribonucleotide is amplified by using the substrate binding sequences as primers. The amplified product is cloned into a eukaryotic expression vector. A ribozyme of the present invention can be expressed in eukaryotic cells from the appropriate DNA vector. If desired, the activity of the ribozyme may be augmented by its release from the primary transcript by a second ribozyme (Ohkawa et al., Nucleic Acids Symp. Ser., 27: 15-6 (1992); Taira et al., Nucleic Acids Res., 19: 5125-30 (1991); Ventura et al., Nucleic Acids Res., 21, 3249-55 (1993).

The ribozyme is present in the composition in a concentration effective to inhibit the expression of the nucleic acid encoding a Complex III protein, for example Core 1.

In embodiments in which a nucleic acid encoding a ribozyme is used as an inhibitor, the nucleic acid is one which encodes a ribozyme which is capable of hybridizing with and cleaving mRNA encoding a Complex III protein, for example Core 1. The nucleic acid is present in the composition in a concentration effective to produce a ribozyme in an amount which inhibits the expression of the protein. This may be determined by those of ordinary skill in the art.

In embodiments in which a small molecule compound which inhibits the activity of a Complex III protein, for example Core 1, is used, the compound is one which sensitizes cells to TRAIL-induced apoptosis by inhibiting the function of the mitochondrial complex III, for example, by inhibiting activity of the aforementioned protein. The small molecule compound is present in the composition in a concentration effective to inhibit the activity of the Complex III protein, for example Core 1, or enhance the effect of TRAIL on tumor cells irrespective of the activity of the Complex III protein in these cells.

In embodiments in which a nucleic acid encoding a small molecule compound is used, the nucleic acid is one which encodes a small molecule compound which inhibits the TNF-suppressing activity of a Complex III protein, for example Core 1. The nucleic acid is present in the composition in a concentration effective to produce the aforementioned compound in an amount which inhibits the activity of the protein. This may be determined by those of ordinary skill in the art.

In the above embodiments which involve the use of a nucleic acid which encodes an antisense nucleic acid or a protein, for example, an antibody, a ribozyme, or a small molecule, that is used to inhibit the TNF-suppressing activity of a Complex III protein, for example Core 1, the nucleic acid may comprise also one or more regulatory regions which regulate the expression of the coding portion of the nucleic acid. Selection of the appropriate regulatory region or regions is a routine matter and is within the level of ordinary skill in the art. Regulatory regions include promoters, enhancers, suppressors, etc.

Promoters that may be used in the present invention include both constitutive promoters and regulated (inducible) promoters. Examples of promoters useful for practice of this invention are: ubiquitous promoters (e.g. HPRT, vimentin, actin, tubulin); intermediate filament promoters (e.g. desmin, neurofilaments, keratin, GFAP); therapeutic gene promoters (e.g. MDR type, CFTR, factor VIII); and tissue-specific promoters (e.g. actin promoter in smooth muscle cells, or Flt and Flk promoters active in endothelial cells).

Tissue-specific promoters include transcriptional control regions which exhibit tissue specificity, for example: elastase I gene control region which is active in pancreatic acinar cells (Swift et al., 1984, Cell 38:639-646; Ornitz et al., 1986, Cold Spring Harbor Symp. Quant. Biol., 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol., 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol., 5:1639-1648; Hammer et al., 1987, Science 235:53-58), alpha 1-antitrypsin gene control region which is active in the liver (Kelsey et al., 1987, Genes and Devel., 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314: 283-286), and gonadotropic releasing hormone gene control region which is active in the hypothalamus (Mason et al., 1986, Science 234:1372-1378).

Other promoters which may be used in the practice of the invention include, for example, promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in International Application Publication No. WO 96/01313 and U.S. Pat. Nos. 5,168,062 and 5,385,839.

In an embodiment of the present invention, the composition comprises a vector which, in turn, comprises the above-described nucleic acid. A vector is any means for the transfer of a nucleic acid into a cell. The term "vector" includes both viral and non-viral means for introducing the nucleic acid into a cell. Non-viral vectors include, for example, plasmids, liposomes, electrically charged lipids (cytofectins), DNA-protein complexes, and biopolymers. Viral vectors include, for example, retrovirus, adeno-associated virus, pox, baculovirus, vaccinia, herpes simplex, Epstein-Barr and adenovirus vectors. In addition to a nucleic acid, the vector may also contain one or more selectable markers useful in selecting, measuring, and monitoring nucleic acid transfer results (transfer to which tissues, duration of expression, etc.).

With respect to the use of a viral vector, it may be replication defective, that is, it is unable to replicate autonomously in the target cell. In general, the genome of the replication defective viral vectors lacks at least one region which is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion, or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles With respect to the use of retroviruses, they are integrating viruses which infect dividing cells. The retrovirus genome includes two LTRs, an encapsidation sequence, and three coding regions (gag, pol and env). The construction of recombinant retroviral vectors has been described in, for example, European Patent Nos. 453242 and 178220 and in Bernstein et al., Genet. Eng., 7: 235 (1985) and McCormick, BioTechnology, 3: 689 (1985). In recombinant retroviral vectors, the gag, pol and env genes are generally deleted, in whole or in part, and replaced with a heterologous nucleic acid sequence of interest. These vectors can be constructed from different types of retrovirus, such as, MoMuLV ("murine Moloney leukaemia virus"), MSV ("murine Moloney sarcoma virus"), HaSV ("Harvey sarcoma virus"), SNV ("spleen necrosis virus"); RSV ("Rous sarcoma virus"), and Friend virus. Lentivirus vector systems may also be used in the practice of the present invention. The lentiviral genome is a positive-strand polyadenylated RNA of 9,000 to 10,000 base pairs containing three structural genes organized 5' to 3' (gag, pol, env), typical of all retroviruses. For an extensive review of lentiviral systems, see Fields Virology, Second Edition, Volume 2, Chapter 55, "Lentiviruses," pp. 1571-1589, Raven Press, New York, 1990.

In general, in order to construct recombinant retroviruses containing a nucleic acid of the present invention, a plasmid is constructed which contains the LTRs, the encapsidation sequence and the coding sequence. This construct is used to transfect a packaging cell line which is capable of supplying in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (International Application Publication No. WO090/02806) and the GP+envAm-12 cell line (International Application Publication No. WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

With respect to the use of adeno-associated viruses (AAV), they are DNA viruses of relatively small size which can integrate, in a stable and site-specific manner, into the genome of the cells which they infect. They are able to infect a wide spectrum of cells without inducing any effects on cellular growth, morphology or differentiation, and they appear to not be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see International Application Publication Nos. WO 91/18088 and WO 93/09239; U.S. Pat. Nos. 4,797,368 and 5,139,941; and European Patent No. 488528). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs utilized in the present invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example, an adenovirus). The AAV recombinants which are produced are then purified by standard techniques.

In a preferred embodiment, the vector utilized in the present invention is an adenovirus vector. Adenoviruses are eukaryotic DNA viruses that can be modified to efficiently deliver a nucleic acid to a variety of cell types.

Various serotypes of adenovirus exist. Preferred serotypes for use in the practice of the present invention are type 2 or type 5 human adenoviruses (Ad 2 or Ad 5) or adenoviruses of animal origin (see International Application Publication No. WO 94/26914). Adenoviruses of animal origin include, for example, adenoviruses of canine, bovine, murine (example: Mav1, Beard et al., Virology 75: 81 (1990)), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors comprise the ITRs, an encapsidation sequence, and the nucleic acid of interest. Still more preferably, at least the E1 region of the adenoviral vector is non-functional. The deletion in the E1 region preferably extends from nucleotides 455 to 3329 in the sequence of the Ad5 adenovirus. Other regions may be modified also, in particular: the E3 region (see International Application Publication No. WO 95/02697); the E2 region (see International Application Publication No. WO 94/28938); the E4 region (see International Application Publication Nos. WO 94/28152, WO 94/12649 and WO 95/02697), or in any of the late genes L1-L5. Defective retroviral vectors are disclosed in International Application Publication No. WO 95/02697.

In a preferred embodiment, the adenoviral vector has a deletion in the E1 and E4 regions. In another preferred embodiment, the adenoviral vector has a deletion in the E1 region into which the E4 region and the sequence encoding the nucleic acid of interest are inserted (see French Publication No. 94 13355).

Any suitable technique can be used to prepare replication defective recombinant adenoviruses. Exemplary techniques are described in Levrero et al., Gene 101:195 (1991); European Patent No.185 573; and Graham, EMBO J., 3: 2917 (1984). In particular, the adenoviruses can be prepared by homologous recombination between an adenovirus and a plasmid which carries, inter alia, the nucleic acid of interest. The homologous recombination is effected following co-transfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which can be used are the human embryonic kidney cell line 293 (see Graham et al., J. Gen. Virol., 36: 59 (1977)) which contains the left-hand portion of the genome of an Ad5 adenovirus (12%) integrated into its genome, and cell lines which are able to complement the E1 and E4 functions, as described in International Application Publication Nos. WO 94/26914 and WO 95/02697. Recombinant adenoviruses are recovered and purified using standard molecular biological techniques, which are well known to one of ordinary skill in the art.

Certain non-viral systems have been used in the art and can facilitate introduction of nucleic acid into a cell.

A nucleic acid can be introduced into a cell by lipofection, for example, using a liposome. The use of cationic lipids may promote encapsulation of negatively charged nucleic acids and also promote fusion with negatively charged cell membranes (see Felgner and Ringold, Nature 337:387-388 (1989)). Particularly useful lipid compounds and compositions for transfer of nucleic acids are described in International Application Publication Nos. WO 95/18863 and WO 96/17823 and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically.

Other molecules are also useful for facilitating transfection of a nucleic acid in vivo, for example, a cationic oligopeptide (see, e.g., International Patent Application Publication No. WO 95/21931), peptides derived from DNA binding proteins (see, e.g., International Patent Application Publication No. WO 96/25508), and a cationic polymer (see, e.g., International Patent Application Publication No. WO 95/21931).

It is also possible to introduce a nucleic acid into a cell as a naked nucleic acid vector (see U.S. Pat. Nos. 5,693,622; 5,589,466; and 5,580,859). Naked nucleic acid vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson et al., J. Biol. Chem. 267:963-967 (1992); Wu and Wu, J. Biol. Chem. 263: 14621-14624 (1988); Hartmut et al., Canadian Patent No. 2,012,311; Williams et al., Proc. Natl. Acad. Sci. USA 88:2726-2730 (1991)). Receptor-mediated DNA delivery approaches can also be used (Curiel et al., Hum. Gene Ther. 3:147-154 (1992); Wu and Wu, J. Biol. Chem. 262:4429-4432 (1987)).

The present invention provides compositions which comprise the inhibitor of the present invention and a carrier. The carrier is one in which the inhibitor is maintained in an active form, e.g., in a form able to effect a biological activity. For example, a nucleic acid would be able to replicate, translate a message, or hybridize to a complementary nucleic acid; a vector would be able to transfect a target cell; an antibody would bind Core 1. Generally, such a carrier will be an aqueous buffer, e.g., Tris, phosphate, or HEPES buffer, containing salt ions. Usually the concentration of salt ions will be similar to physiological levels. For guideline purposes, it is believed most applications will involve the use of a carrier in an amount of from 40 to about 98% by weight of the composition. In some embodiments, the carrier is present in an amount of about 50 to about 98% by weight of the composition.

The composition may comprise also stabilizing agents, preservatives, and other excipients.

The composition of the present invention can be formulated for administration by oral and parenteral means (e.g., topical, intranasal, subcutaneous, and intraocular routes). Parenteral administration is meant to include intravenous injection, intramuscular injection, intraarterial injection or infusion techniques. The composition may be administered parenterally in dosage unit formulations containing standard, well known nontoxic physiologically acceptable carriers, adjuvants and vehicles as desired.

The preferred sterile injectable preparations can be a solution or suspension of the inhibitor in a nontoxic parenterally acceptable carrier. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The carrier can also be a hydrogel which is prepared from any biocompatible or non-cytotoxic (homo or hetero) polymer, such as a hydrophilic polyacrylic acid polymer that can act as a sponge onto which the inhibitor is absorbed. Such polymers have been described, for example, in International Application Publication No. WO 93/08845. A hydrogel can be deposited directly onto the surface of the tissue to be treated.

Another preferred embodiment of the present invention includes a pharmaceutical composition comprising a poloxamer, as the carrier, which is impregnated with a replication defective recombinant virus that comprises a nucleic acid according to the present invention. A preferred poloxamer is Poloxamer 407, which is commercially available (BASF, Parsippany, N.J.) and is a non-toxic, biocompatible polyol. Poloxamers possess essentially the same advantages as hydrogels while having a lower viscosity.

The present invention provides a method of treatment which comprises the administration to a human or other animal of an effective amount of a composition of the present invention. Effective amounts of the composition may vary, depending on the age, type and severity of the condition to be treated, body weight, desired duration of treatment, method of administration, and other parameters. Effective amounts are determined by a physician or other qualified medical professional.

The present invention provides also a method for assaying compounds to determine if they are capable of functioning as inhibitors of the TNF-suppressing activity of a Complex III protein, for example Core 1. In the assay, the viability of cells which express a Complex III protein, for example Core 1, and that are known to be naturally resistant to TNF-induced apoptosis and that have been contacted with both a member of the TNF superfamily (hereafter "TNF") and the compound is compared with the viability of control cells which are from the same cell line and which also express the protein and that have been contacted with the compound but not with TNF. Viability may be determined using the Cell Titer Blue Assay, which measures the metabolic capacity (and thus viability) of a cell by its ability to reduce the dye resazurin to its highly fluorescent form resorufin, which may be detected using a spectrophotometer.

If the compound reduces significantly the viability of both the cells that have been contacted with TNF and the control cells, the activity of the compound is considered to be not related to TNF and the compound is not considered a compound of interest. If the compound significantly reduces the viability of the cells that have been contacted with TNF but not the viability of the control cells, then it is considered to sensitize the cells to the apoptotic activity of TNF as the cell line had been known previously to be resistant to TNF. As the cell expresses the Complex III protein, it is inferred that the compound assayed acts by inhibiting the TNF-suppressing activity of the Complex III protein.

A compound is considered to reduce significantly the viability of a cell when the viability of the cells that were contacted with TRAIL and the compound assayed have a minimum of about 30% lower viability as compared to the viability of the control cells.

In an embodiment of the present invention, cells which express a Complex III protein, for example Core 1, and which are from a cell line that is known to be naturally resistant to TNF-induced apoptosis are grown in the presence of TNF, for example, for 24 hours, and then contacted with the compound to be assayed. Control cells from the same cell line are grown in the absence of TNF for the same period of time and contacted with the same compound. The viability of the cells is then measured and compared.

Essentially any cell line known to be naturally resistant to TRAIL-induced apoptosis and which expresses the Complex III protein of interest or has been modified to express the protein, for example, by transfection of a transgene which expresses the protein, may be used in the conduct of this assay. An example of such a cell line is the HCT116 colon tumor cell line which has been engineered to stably express Core 1. The Core 1 transgene may be introduced, for example, by infection of the HCT116 cell utilizing the standard lentiviral or retroviral or adenoviral expression vectors used in the field. The present invention contemplates also that the cell need not express an entire protein, as long as it expresses the portion of the protein that confers the ability to suppress the apoptotic-inducing activity of TNF. Accordingly, the cell may contain or be modified to contain only a nucleic acid that encodes such a portion of the Complex III protein.

A cell may be exposed to the compound being assayed at a nanomolar to micromolar range of concentration for 24 to 96 hrs at 37° C. and the viability of the cells measured by using commercially available assays, for example, WST-1, MTT, and caspase-3 assays. The effect of the compounds on cell cycle progression may be measured by FACS analysis or by other standard image based assays used in the field. All the compound based experiments described may also be performed under hypoxic conditions (1-2% oxygen) to examine whether hypoxic conditions enhance or induce cell death in the presence of TRAIL.

Cells may be exposed to TRAIL by direct addition of TRAIL in an appropriate carrier solution (e.g. phosphate buffered saline) to a receptacle containing the cell at a concentration of about 50 to about 200 ng/ml and growing the cell in the presence thereof for up to about 96 hours.

EXAMPLES

Example 1

This example describes the discovery that Core 1 is involved in resistance to TRAIL-mediated apoptosis.

Figure 1A:
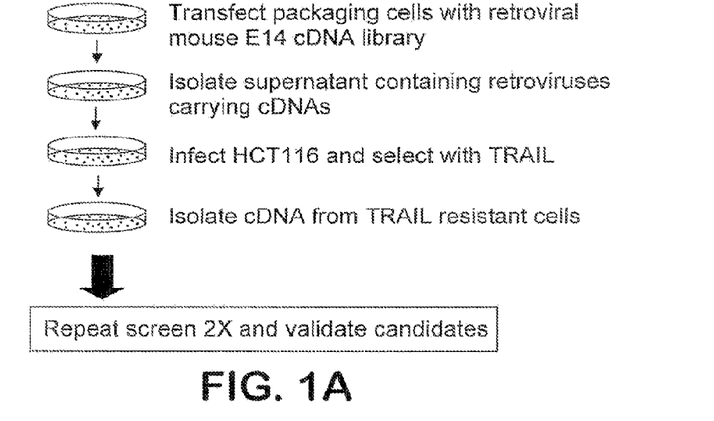
FIG. 1A is a flow chart describing a method for screening a cDNA library for genes which confer resistance to TRAIL-induced apoptosis. Schematic diagram shows a genetic screen of a mouse E14 cDNA library for resistance to TRAIL induced apoptosis. cDNAs from TRAIL resistant cells were isolated, sequenced and validated.

A functional genetic screen of a mouse E14 cDNA library g HCT116 colon carcinoma line, a cell line known to be sensitive to TRAIL-induced apoptosis, was conducted [FIG. 1A]. The screen identified UQCRC1, which encodes Core 1, as being involved in resistance to TRAIL-mediated apoptosis.

HCT116 cells (American Type Culture Collection, Manassas, Va.) and 293 EBNA packaging cell line (Invitrogen) were grown separately in Dulbecco's modified Eagle's Medium (DMEM) with 10% heat-inactivated fetal bovine serum (FBS) and 1% penicillin-streptomycin (Gibco) at 37° C. and 5% $CO_2$.

A mouse embryonic day-14 retroviral cDNA library (gift of George Daley, MIT, Cambridge, Mass.) was cloned into pEYK retroviral vector and transfected into the above 293 EBNA packaging cell line using Lipofectamine (Invitrogen). Forty-eight to 72 hours after the transfection, the supernatant was collected. The supernatant was mixed with 10 mg/mL polybene and used to infect the above HCT116 cells which had been plated 48 hours before infection. After 48 hours of infection, $1.0 \times 10^6$ cells were plated in 15 cm dishes and treated with 200 ng/mL recombinant human TRAIL (Bio-Mol, Plymouth Meeting, Pa.) for 10 days, with fresh media and TRAIL being added every 48 hours. Individual clones resistant to TRAIL-induced apoptosis were harvested.

Figure 1B:
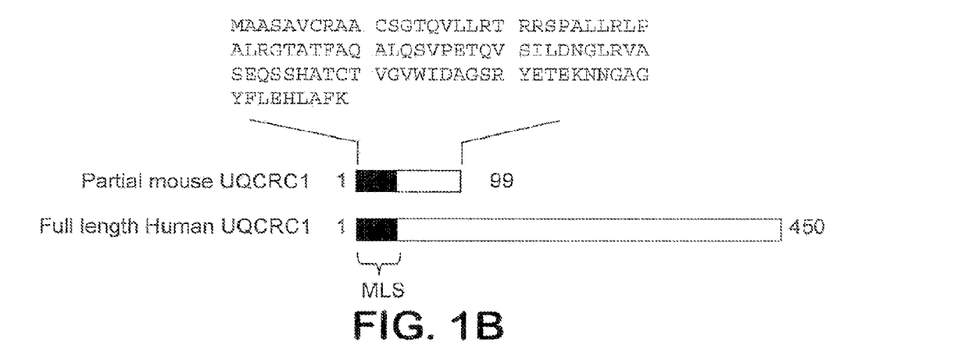
FIG. 1B shows a partial amino acid sequence of mouse UQCRC1 (Core 1) cDNA as compared with full length human UQCRC1 cDNA(SEQ ID NO: 3). Both contain a mitochondrial localization sequence (MLS).
Figure 1C:
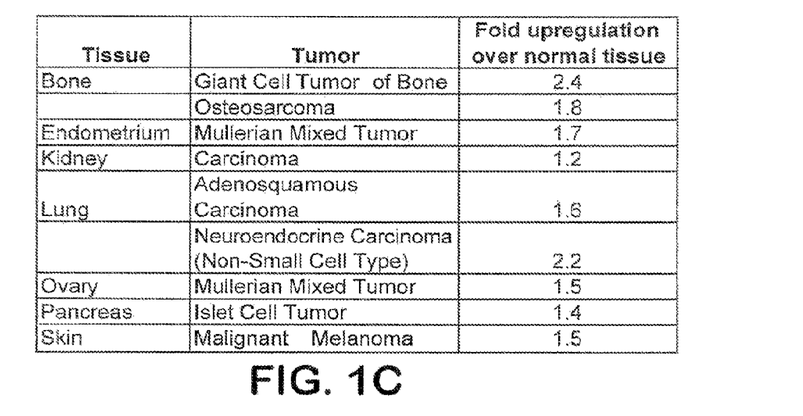
FIG. 1C is a chart showing the level of overexpression of Core 1 in various tumor tissues (data from Ascenta database).

Genomic DNA was isolated from the resistant clone by resuspending the cells in digestion buffer (100 nM NaCl, 10 mM Tris pH 8, 25 mM EDTA, 0.5% SDS) followed by proteinase K treatment at a final concentration of 100 μg/ml at 50° C. for 12 hr. Samples were extracted by phenol-chloroform and ethanol precipitation. Candidate cDNAs were then amplified using library-specific primers, or the recovered retroviral plasmid was used directly to perform another iteration of the screen. One of the interesting candidate cDNAs found as potentially conferring resistance to TRAIL-induced apoptosis was the cDNA for ubiquinol cytochrome c reductase core subunit 1 (UQCRC1), which encodes Core 1 [FIG. 1B].

Example 2

Figure 2A:
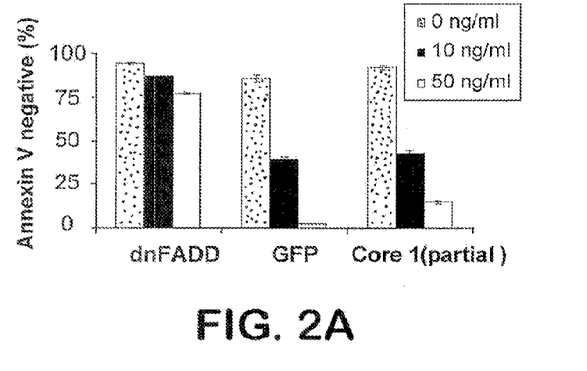
FIG. 2A is a bar graph showing the viability (as measured by the percentage of cells that are Annexin V negative) of HCT116 cells expressing dominant negative FADD (dn-FADD), Green Florescent Protein (GFP), or partial Core 1 that have undergone treatment by TRAIL at 10 ng/ml or 50 ng/ml or no treatment by TRAIL (0 ng/ml).

To further characterize the ability of Core 1 to protect against TRAIL-induced apoptosis, the pEYK vector containing the partial cDNA of UQCRC1 isolated from the screen was used to directly infect HCT116 cells. Cells expressing dominant-negative FADD (dnFADD), which inhibits the signal from the TRAIL receptors, was used as a control. Cells were treated for 48 hours with 0, 10 or 50 ng/mL of TRAIL and assayed for Annexin V, an early marker of apoptosis [FIG. 2A]. Expression of dnFADD inhibited TRAIL-induced apoptosis, with 78% of cells Annexin V negative or non-apoptotic at 50 ng/ml TRAIL. In cells expressing Green Fluorescent Protein (GFP), only 2% were Annexin V negative at 50 ng/ml, compared to 14.5% in Core 1 expressing cells, a 7 fold increase in protection from TRAIL induced apoptosis. This suggests that expression of the partial Core 1 protein provides some protection, but does not completely inhibit TRAIL induced apoptosis.

Example 3

As Core 1 is a subunit of the mitochondrial respiratory Complex III, work was conducted to determine whether expression of Core 1 protects against mitochondrial depolarization, a critical step in mitochondrial mediated apoptosis. Changes in mitochondrial membrane potential during TRAIL treatment were studied using the JC-1 Assay Kit (Molecular Probes). JC-1 (5, 5',6,6',-tetrachloro-1,1',3,3'-tetraethylbenz-imidazolylcarbocyanine) is a cationic dye which has a diffuse green fluorescence in the cytoplasm. The accumulation of JC-1 in the mitochondria, which depends on intact, polarized mitochondria, results in the formation of red fluorescent aggregates. The ratio of green to red fluorescence was measured for the cells described in Example 2 above by Fluorescence-activated Cell Sorter (FACS) analysis. FACS is a method to sort cells based on specific cellular surface markers (e.g., red or green fluorescence). The above ratio is plotted as a percentage of polarized mitochondria.

Figure 2B:
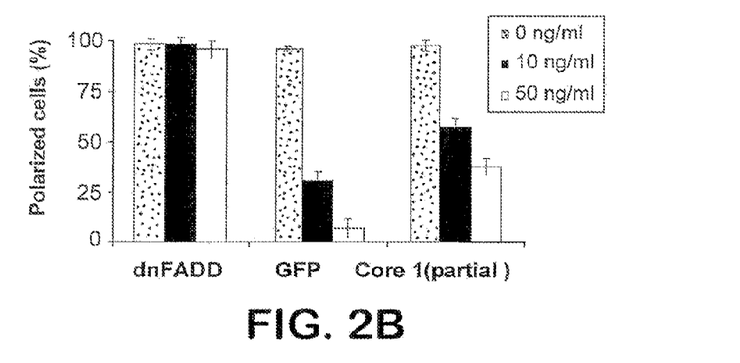
FIG. 2B is a bar graph showing the viability (as measured by the percentage of polarized mitochondria in the cells) of HCT116 cells expressing dominant negative FADD (dn-FADD), Green Florescent Protein (GFP), or partial Core 1 that have undergone treatment by TRAIL at 10 ng/ml or 50 ng/ml or no treatment by TRAIL (0 ng/mL).

Expression of dnFADD completely protected against mitochondrial depolarization at all concentrations of TRAIL, while cells expressing GFP showed only 7% polarized mitochondria remaining at 50 ng/ml of TRAIL. Expression of partial Core 1 showed 38% polarized mitochondria, providing a 5-fold protection from mitochondrial depolarization over GFP [FIG. 2B]. Thus, Core 1 protects also against mitochondrial depolarization.

Example 4

Figure 2C:
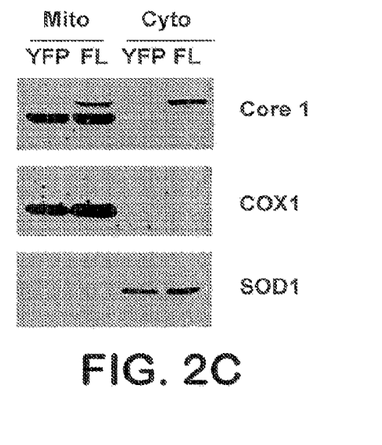
FIG. 2C is a Western blot, performed on cytoplasmic and mitochondria fractions prepared from stable cells lines expressing Yellow Florescent Protein (YFP) or full length human Core 1 (FL), using antibodies for Core 1, COX 1 (a mitochondrial marker), and SOD1 (a cytoplasmic marker).
Figure 2D:
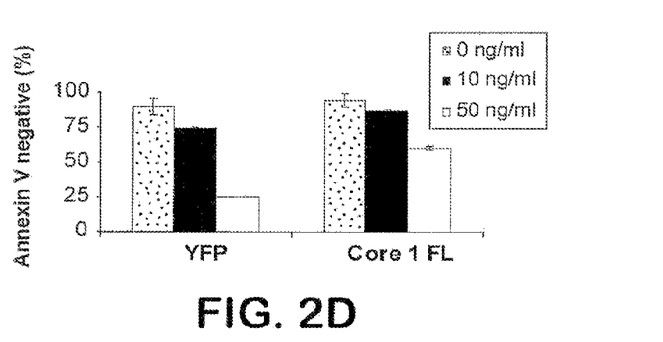
FIG. 2D is a bar graph showing the viability (as measured by the percentage of cells that are Annexin V negative) of HT116 cells expressing Yellow Florescent Protein (YFP) or full length human Core 1 that have undergone treatment by TRAIL at 10 ng/ml or 50 ng/ml or no treatment by TRAIL (0 ng/ml).

To confirm that the protection observed from the partial Core 1 protein is indicative of its function, the full length human Core 1 protein was cloned into the pLenti-vector (containing a HA-tag) and used to infect HCT116 to produce a stable cell line expressing Core 1. A control cell line was prepared similarly to express Yellow Fluorescent Protein (YFP). To confirm the protein expression of full length Core 1, cells were homogenized to prepare a mitochondrial and cytoplasmic lysate and western blotted with antibodies to Core 1 [FIG. 2C]. The endogenous Core 1 is detected in the mitochondrial fraction of both YFP and Core 1 expressing cells. Exogenously expressed Core 1 is HA-tagged and is detected as a higher migrating band in the mitochondrial fraction, as well as the cytoplasmic fraction. This expression pattern is not the result of contamination of the cytoplasmic fraction with mitochondrial proteins, as COX1 (Complex IV subunit 1) is detected only in the mitochondrial fraction, whereas SOD1 (SuperOxide Dismutase 1), a cytoplasmic marker, does not detect cytoplasmic proteins in the mitochondrial fraction. Thus, Core 1 is expressed in these HCT116 stable cell lines. To determine if full length Core 1 also protects against TRAIL-induced apoptosis, cells were treated with TRAIL and assayed for apoptosis by FACS analysis for cells that were Annexin V positive or negative. Core 1 expressing cells showed a 2.5 fold protection against TRAIL-induced apoptosis at 50 ng/ml [FIG. 2D]. These data show that expression of Core 1 in HCT116 protects against TRAIL-induced apoptosis and mitochondrial depolarization.

Example 5

This example demonstrates the inhibitory effect of Core 1 on the activity of caspases 8, 9, and 3.

Figure 3A:
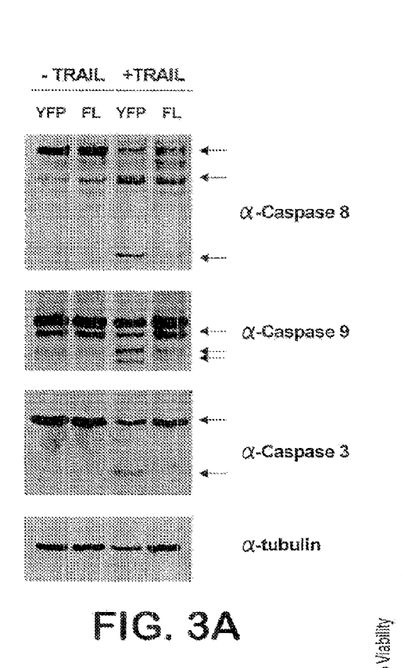
FIG. 3A is a Western blot, performed on fractions prepared from stable HCT116 cells lines expressing Yellow Florescent Protein (YFP) or full length human Core 1 (FL) that have either been treated with 200 ng/ml TRAIL for 24 hours or not treated with TRAIL, using antibodies for Caspase 8, Caspase 9, Caspase 3, and tubulin (blots were stripped and re-probed with antibodies to tubulin as a loading control).

Cells stably expressing YFP or human full length Core 1 were treated for 24 hours with 200 ng/ml TRAIL, lysed, and western blotted with antibodies to several caspases. Caspase activation was detected by the cleavage of the full length pro-caspase to the smaller, active form. HCT116 expressing human full length Core 1 showed less active caspase 8 upon TRAIL stimulation than cells expressing YFP [FIG. 3A]. Furthermore, Core 1 expression resulted similarly in a reduced activation of both caspase 9 and caspase 3. Thus, Core 1 expression inhibits the full activation of caspases 8, 9, and 3 upon TRAIL stimulation.

Example 6

This example demonstrates the effect of Core 1 on the release of cytochrome c from the mitochondria.

Figure 3B:
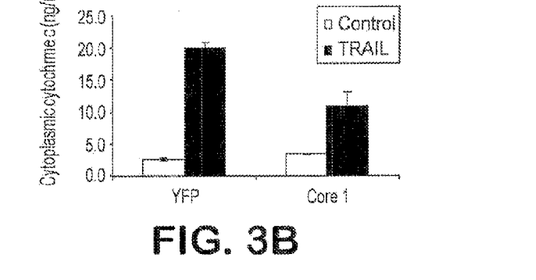
FIG. 3B is a bar graph showing the amount of cytochrome c present in cells that expressing either Yellow Florescent Protein (YFP) or Core 1 that have been treated with 100 ng/ml of TRAIL or not treated with TRAIL (0 ng/ml). The amount of cytochrome c in the lysates was quantified by ELISA.

HCT116 cells stably expressing YFP or human full length Core 1 were treated with 100 ng/ml TRAIL for 24 hours. Control cells stably expressing YFP or human full length Core 1 were not treated with TRAIL. The cells were then harvested. Media containing floating cells was first removed to new tubes. The remaining adherent cells were detached using a cell scraper in ice-cold PBS and added to the media containing floating cells. The cells were pelleted by centrifuging at 1000×g for 10 minutes at 4° C. and resuspended in an iso-osmotic buffer (0.3M sucrose, 10 mM Tris pH 7.5, 1 mM EDTA, EDTA-free protease tablet). After a five minute incubation on ice, the cells were lysed using dounce homogenizers until about 90% of the plasma membranes were lysed. This was done to isolate the cytoplasmic fraction. The extent of cell lysis was monitored by mixing 10 µl of lysate with trypan blue and viewed on a hemocytometer. The supernatant was transferred to fresh tubes and centrifuged at 8000×g for 10 minutes at 4° C. to pellet mitochondria. The concentration of lysates was determined using either the BioRad DC protein assay (BioRad) or the BCA method (Pierce, Rockford, Ill.). To quantitatively detect cytochrome c levels, lysates were assayed for cytochrome c using a Function ELISA cytochrome c kit (Active Motif, Carlsbad, Calif.) [FIG. 3B]. In untreated cells, low baseline levels of cytochrome c were detected in the cytoplasm. Upon treatment with TRAIL, cells expressing YFP had a 10-fold increase in the amount of cytochrome c released into the cytoplasmic fraction, while cells expressing Core 1 released only one-half as much cytochrome c [FIG. 3B]. This work suggests that expression of Core 1 reduces also the amount of cytochrome c released from the mitochondria into the cytosol upon TRAIL treatment.

Example 7

Figure 3C:
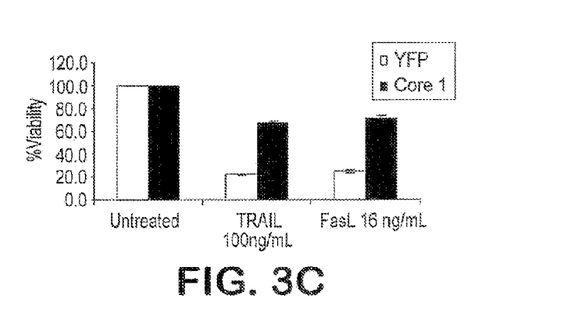
FIG. 3C is a bar graph showing the viability of cells expressing Yellow Florescent Protein (YFP) or Core 1 that have undergone either no treatment or treatment by TRAIL at 100 ng/ml or FasL at 16 ng/ml. Cell viability assayed using Cell Titer Blue.

To determine whether Core 1 protected against apoptosis induced by TRAIL or through other pathways, cells were treated with several different apoptosis inducers and assayed for cell viability. Fas Ligand (FasL), also a TNFα family member which signals through Death Receptors, uses the same adaptor protein FADD to induce caspase activation and apoptosis. Cells stably expressing either yellow florescent protein (YFP) or human full length Core 1 were treated with 100 ng/ml of TRAIL or 16 ng/ml of FasL for 24 hours. Cell viability was assayed using the Cell-Titer Blue assay, where conversion of the indicator dye resazurin is used to measure the metabolic capacity of cells, an indicator of cell viability. Expression of Core 1 offered about a three-fold protection from FasL induced apoptosis similar to TRAIL [FIG. 3C]. This suggests that Core 1 can protect against apoptosis induced by death receptor signaling.

Figure 3D:
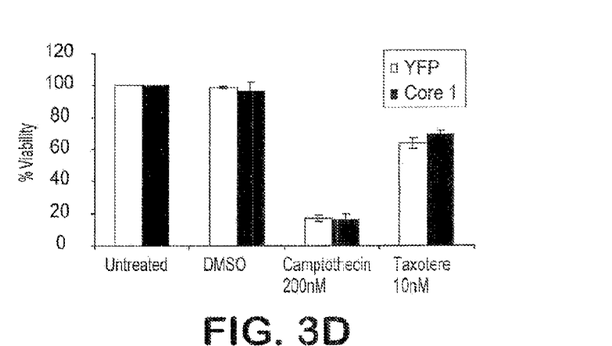
FIG. 3D is a bar graph showing the viability of cells expressing Yellow Florescent Protein (YFP) or full length human Core 1 that have undergone not treatment or treatment by 200 nM Camptothecin, 10 nM Taxotere, or DMSO. Cell viability assayed using Cell Titer Blue.

Cells were then treated with two compounds which induce apoptosis through non-death receptor pathways. Camptothecin inhibits DNA topoisomerase 1, ultimately leading to DNA damage and death, while Taxotere is an inhibitor of microtubule depolymerization, which prevents cell division and leads to mitotic death. No difference in viability between cells expressing YFP or human full length Core 1 was seen upon treatment with either 200 nM Camptothecin in dimethyl sulfoxide or 10 nM Taxotere in dimethyl sulfoxide [FIG. 3D]. These results show that Core 1 does not protect against other non-death receptor mediated apoptosis caused either by DNA damage or inhibition of microtubule depolymerization. These data strongly suggest that Core 1 plays a role in the regulation of TRAIL-induced apoptosis and are consistent with the observation that Core 1 gives partial protection to TRAIL induced apoptosis.

Example 8

This example describes the use of siRNA to inhibit the expression of Core 1.

Figure 4A:
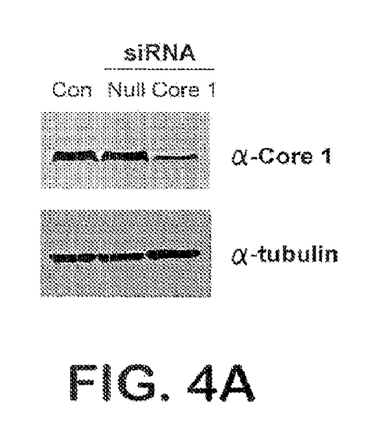
FIG. 4A is a Western blot, performed on fractions prepared from HCT116 wildtype cells that have been incubated with lipofectamine alone (control cells), 3.75 nM Null siRNA, or Core 1 siRNA for 72 hours, using antibodies for Core 1 and tubulin (blots were stripped and re-probed with antibodies to tubulin as a loading control).
Figure 4B:
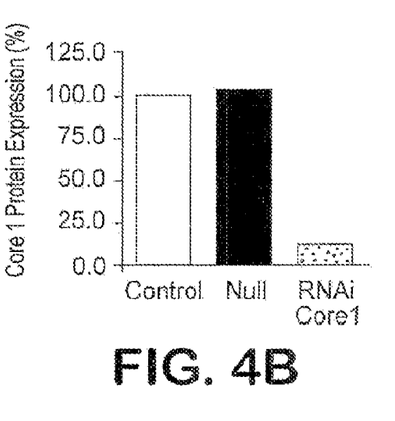
FIG. 4B is a bar graph showing the level of Core 1 expression in each of the cells described for FIG. 4A above.

HCT116 cells containing endogenous Core 1 (and not containing exogenous Core 1) were plated at $1 \times 10^5$ cells per 6-well dish in penicillin/streptomycin-free media for 24 hours prior to transfection. Cells were transfected with Lipofectamine 2000 (Invitrogen) following manufacturer protocols. Cells were incubated for 72 hours with transfection mixture containing Lipofectamine alone (control cells), 3.75 nM siRNAs to UQCRC1 (SMARTpool), or non-targeting siRNA (Null) (Dharmacon, Lafayette, Colo.). Protein concentration was determined by preparing lysates and Western blotting using antibodies to Core 1 [FIG. 4A]. The blots were re-stripped and re-probed using anti-tubulin antibodies as a loading control. Transfection of Core 1 resulted in a 90% reduction of Core 1 protein, while transfection with Lipofectamine alone or the Null siRNA did not affect Core 1 protein levels [FIG. 4B].

Figure 4C:
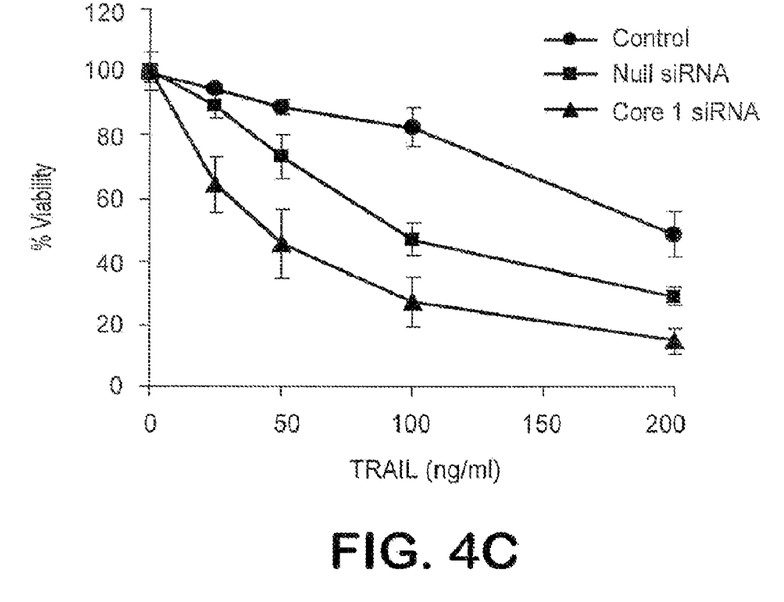
FIG. 4C is a graph showing the viability of cells, previously treated with lipofectamine alone, Null siRNA, or Core 1 siRNA, following treatment with increasing concentrations of TRAIL.

Each of the above groups of cells was then treated with various concentrations of TRAIL for an additional 24 hours and cell viability assayed using the Cell Titer Blue assay (Promega, Madison, Wis.). This assay measures the metabolic capacity of a cell (and thus its viability) by its ability to reduce the dye resazurin to the highly fluorescent resorufin. The amount of Cell Titer Blue reagent (a buffered solution containing highly purified resazurin) added was 20% of the volume of the media. Cells were incubated at 37° C. for 2-3 hours and assayed using a bottom reading fluorescent plate reader at the excitation at 560 nm and the emission at 590 nm. Cells were plated in triplicate. The cells were then washed in 2× cold PBS (Gibco) and lysed in 100 μl ice cold lysis buffer (50 nM HEPES pH 7.4, 250 nM NaCl, 2 nM EDTA, 1% Triton X-100, EDTA-free protease inhibitors (Roche)). Lysates were centrifuged for 10 minutes at 3500 rpm at 4° C. The supernatant was mixed with 4× LDS sample buffer (Invitrogen) and heated at 90° C. for 10 minutes, and stored at −20° C. The results of the assay are shown in FIG. 4C. Results shown are an average of 4 separate experiments. Cells with Core 1 knockdown showed only 60% viability at 25 ng/mL TRAIL, compared to 90-95% at the same concentration in the control or Null transfected cells [FIG. 4C]. Core 1 knockdown cells had less than 50% viability at 50 ng/ml, while it takes two times the amount of TRAIL to induce 50% viability in Null transfected cells. Although transfection of the Null siRNA alone appears to have an effect on sensitivity to TRAIL over Lipofectamine alone, this data clearly demonstrates that reduction of Core 1 protein sensitizes cells to TRAIL induced apoptosis, especially at lower concentrations. These data support strongly that Core 1 has a role in regulating TRAIL-induced apoptosis.

Example 9

This example describes an assay to determine whether a compound inhibits Core 1 activity.

The compound to be assayed is added at 10 μM concentration in a suitable carrier (e.g., dimethyl sulfoxide, ethanol, buffered saline) to HCT116 cells (American Type Culture Collection, Manassas, Va.) which were pre-infected with Core 1 DNA. The cells are then grown in Dulbecco's modified Eagle's Medium (DMEM) with 10% FBS in the presence of an appropriate concentrations of up to 200 ng/ml of TRAIL and kept for 24 hrs. The compound is added also at 10 μM concentration to HCT116 cells which were pre-infected with Core 1 DNA. The cells are then grown in DMEM with 10% FBS in the absence of TRAIL (control cells) and kept for 24 hrs.

The cells are then washed in PBS and the viability of these cells is measured using the WST-1 assay. The WST-1 assay measures cell viability by measuring the reduction of the chemical substrate WST into a soluble formazan salt, which is detectable by a spectrophotomers. The Cell Titer Blue assay may be used as an alternative to the WST-1 assay. If the compound significantly reduces the viability of both the cells that were grown in the presence of TRAIL and the control cells which were grown in the absence of TRAIL, the activity of the compound is considered to be not related to TRAIL and the compound is not considered a compound of interest. If the compound reduces significantly the viability of the cells that were grown in the presence of TRAIL but not the viability of the control cells, then it is considered to sensitize the cell to the apoptotic activity of TRAIL as the HCT116 cell line expressing Core 1 is known previously to be resistant to TRAIL. As it was known previously also that the cell's resistance to TRAIL-induced apoptosis is caused by Core 1, it is inferred that the compound assayed acts by suppressing the TRAIL-suppressing activity of Core 1.

The invention claimed is:

1. A composition comprising:
 (A) an inhibitor of a Core 1 protein having the amino acid sequence of SEQ ID NO: 2;
 (B) a member of the tumor necrosis factor superfamily; and
 (C) a carrier;
 wherein the inhibitor of Core 1 is a nucleic acid molecule.

2. The composition according to claim 1, wherein the inhibitor is an antisense nucleic acid which inhibits the expression of the gene encoding Core 1.

3. The composition according to claim 1, wherein the inhibitor is a nucleic acid which encodes an antisense nucleic acid which inhibits the expression of the gene encoding Core 1.

4. The composition according to claim 3, wherein the nucleic acid includes a promoter region.

5. The composition according to claim 3, wherein the nucleic acid is contained in a vector.

6. A composition according to claim 1, wherein the inhibitor is an siRNA which inhibits the expression of the gene encoding the Core 1 protein.

7. A composition according to claim 1, wherein the inhibitor is a nucleic acid which encodes an antibody that is capable of binding to and lowering the activity of the Core 1 protein.

8. A composition according to claim 7, wherein the nucleic acid includes a promoter.

9. A composition according to claim 7, wherein the nucleic acid is contained in a vector.

10. A composition according to claim 1, wherein the inhibitor is a ribozyme that is capable of lowering the expression of the Core 1 protein.

11. A composition according to claim 1, wherein the inhibitor is a nucleic acid which encodes a ribozyme that is capable of lowering the expression of the Core 1 protein.

12. A composition according to claim 11, wherein the nucleic acid includes a promoter.

13. A composition according to claim 11, wherein the nucleic acid is contained in a vector.

14. The composition according to claim 1, wherein the member of the tumor necrosis factor superfamily is TRAIL.

15. The composition according to claim 1, wherein the member of the tumor necrosis factor superfamily is Fas ligand.

16. A method for treating a tumor in a patient comprising the step of administering to said patient the composition of claim 1;
 wherein the inhibitor of Core 1 inhibits the expression of the gene encoding Core 1 or the activity of Core 1 protein, thereby treating the tumor in the patient.

17. A method according to claim 16, wherein the member of the tumor necrosis factor superfamily is TRAIL.

18. A method according to claim 16, wherein the member of the tumor necrosis factor superfamily is Fas ligand.

19. A method for making the composition of claim 1, comprising mixing the inhibitor of a Core 1 protein having the amino acid sequence of SEQ ID NO: 2, the carrier, and the member of the tumor necrosis factor superfamily; wherein the inhibitor of Core 1 is a nucleic acid molecule.

* * * * *